US006541683B1

(12) United States Patent
Yanofsky et al.

(10) Patent No.: US 6,541,683 B1
(45) Date of Patent: Apr. 1, 2003

(54) METHOD OF DECREASING SEED SIZE IN A PLANT

(75) Inventors: Martin F. Yanofsky, San Diego, CA (US); Robert Martienssen, Cold Spring Harbor, NY (US); Cristina Ferrandiz, San Diego, CA (US); Qing Gu, Knoxville, TN (US)

(73) Assignees: The Regents of the University of California, Oakland, CA (US); Cold Spring Harbor Laboratory, Cold Spring Harbor, NY (US)

( * ) Notice: Subject to any disclaimer, the term of this patent is extended or adjusted under 35 U.S.C. 154(b) by 52 days.

(21) Appl. No.: 09/708,584

(22) Filed: Nov. 7, 2000

Related U.S. Application Data

(62) Division of application No. 09/105,652, filed on Jun. 26, 1998, now Pat. No. 6,229,068.
(60) Provisional application No. 60/051,030, filed on Jun. 27, 1997.

(51) Int. Cl.$^7$ .................. C12N 15/82; C12N 15/90; C12N 5/04; A01H 5/00; A01H 5/10
(52) U.S. Cl. .................. 800/290; 435/468; 800/285; 800/286; 800/287; 800/298
(58) Field of Search .................. 435/410, 419, 435/468; 800/278, 290, 295, 298, 285, 286, 287

(56) References Cited

U.S. PATENT DOCUMENTS 6,288,305 B1 * 9/2001 Yanofsky et al. ........... 800/290

FOREIGN PATENT DOCUMENTS

WO    WO 98/22592    5/1998    .......... C12N/15/29

OTHER PUBLICATIONS

Altschul et al, Nucl. Acids Res., vol. 25, pp. 3389–3402. 1997.*
Purugganan, M.D., J. Mol. Evol., vol. 45, pp. 392–396. 1997.*
Mena et al, Plant J., vol. 8, pp. 845–854. 1995.*
Mandel et al, "A gene triggering flower formation in Arabidopsis", Oct. 1995, vol. 377, pp. 522–524.*
Aukerman et al., "An arginine to lysine substitution in the bZIP domain of an opaque–2 mutant in amize abolishes specific DNA binding," *Genes & Development* 5:310–320 (1991).
Burr et al., "Zein Storage Protein Gene Family of Maize," *J. Molecular Biology* 154:33–49 (1982).
Colombo et al., "Downregualtion of Ovule–Specific MADS Box Genes from Petunia Results in Maternally Controlled Defects in Seed Development," *The Plant Cell* 9:703–715 (1997).

Flanagan et al., "Specific expression of the AGL1 MADS–box gene suggests regulatory functions in *Arabidopsis gynoecium* and ovule development," *The Plant Journal* 10:343–353 (1996).
GenBank accession 000375 Jun. 1997.
Gillaspy et al., "Fruits: A Developmental Perspective," *The Plant Cell* 5:1439–1451 (1993).
Goldberg et al., "Plant Embryogenesis: Zygote to Seed," *Science* 266:605–614 (1994).
Gu et al., "The Furitfull MADS–box gene mediates cell differentiation during Arabidopsis fruit development," *Development* 125:1509–1517 (1998).
Heck et al., "AGL15, a MADS Domain Protein Expressed in Developing Embryos," *The Plant Cell* 1271–1282 (1995).
Hempel et al., "Floral determination and expression of floral regulatory genes in Arabidopsis," *Development* 124:3845–3853 (1997).
Kempin et al., "Targeted disruption in Arabidopsis," *Nature* 389:802–803 (1997).
Long et al., "A member of the Knotted class of homeodomain proteins encoded by the STM gene of Arabidopsis," *Nature* 379:66–69 (1996).
Ma et al., "AGL1–AGL6, An Arabidopsis gene family with similarity to floral homeotic and transcription factor genes," *Genes & Development* 5:484–495 (1991).
Mandel and yanofsky, "The Arabidopsis AGL8 MADS Box Gene Is Expressed in Inflorescence Meristems and Is Negatively Regulated by APETALA1," *The Plant Cell* 7:1763–1771 (1995).
Menzel et al., "Identification of two MADS box genes that are expressed in the apical meristem of the long–day *Sinapis alba* in transition to flowering," *The Plant Journal* 9:399–408 (1996).
Mizukami et al., "Functional Domains of the Floral Regulator AGAMOUS: Characterization of the DNA Binding Domain and Analysis of Dominant Negative Mutations," *The Plant Cell* 8:831–845 (1996).

(List continued on next page.)

Primary Examiner—Amy J. Nelson
Assistant Examiner—Ashwin Mehta
(74) Attorney, Agent, or Firm—Townsend and Townsend and Crew LLP

(57) ABSTRACT

The present invention provides a non-naturally occurring seed plant that is characterized by producing seeds of increased size due to ectopic expression of a nucleic acid molecule encoding an AGL8-related gene product. The AGL8-related gene product can have, for example, substantially the amino acid sequence of an AGL8 ortholog such as Arabidopsis AGL8 (SEQ ID NO:2). The present invention further provides a non-naturally occurring seed plant that is characterized by producing fruit of increased size due to ectopic expression of a nucleic acid molecule encoding an AGL8-family gene product. The AGL8-family gene product can have substantially the amino acid sequence of an AGL8 ortholog, for example, the amino acid sequence of Arabidopsis AGL8 (SEQ ID NO:2). Related methods and kits also are provided.

18 Claims, 1 Drawing Sheet

OTHER PUBLICATIONS

Perry et al., "The MADS Domain Protein AGL15 Localizes to the Nucleus during Early Stages of Seed Development," *The Plant Cell* 8:1977–1989 (1996).

Purugganan et al., "Molecular Evolution of Flower Development: Diversification of the Plant MADS–Box Regulatory Gene Family," *Genetics* 140:345–356 (1995).

Riechmann and Meyerowitz, "MADS Domain Proteins in Plant Development," *Biol. Chem.* 378:1079–1101 (1997).

Savidge et al., "Temporal Relationship between the Transcription of Two Arabidopsis MADS Box Genes and the Floral Organ Identity Genes," *The Plant Cell* 7:721–733 (1995).

Schmidt et al., "Maize regulatory gene opague–2 encodes a protein with a "leucine–zipper" motif that binds to zein DNA," *Proc. Natl. Acad. Sci. USA* 87:46–50 (1990).

Sundaresan et al., "Patterns of gene action in plant development revealed by enhancer trap and gene trap transposable elements," *Genes Devel.* 9:1797–1810 (1995).

West and Harada, "Embryogenesis in Highe Plants: An Overview," *The Plant Cell* 5:1361–1369 (1993).

Yanofsky, Floral Meristems to Floral Organs: Genes Controlling Early Events in Arabidopsis Flower Development, *Annual Rev. Plant Physiol. Mol. Biol.* 46:167–188 (1995).

Yanofsky et al., "The protein encoded by the *Arabidopsis homeotic* gene agamous resembles transcription facotrs," *Nature* 346:35–39 (1990).

Hempel, et al., "Floral determination and expression of floral regulatory genes in Arabidopsis"; *Development* vol. 124, 3845–3853 (1997).

Mandel, et al., "The Arabidopsis AGL8 MADS Box Gene Is Expressed in Inflorescence Meristems and Is Negatively Regulated by APETALA1";*The Plant Cell* vol. 7, pp. 1763–1771 (1995).

Menzel, et al., "Identification of two MADS box genes that are expressed in the apical meristem of the long–day plant *Sinapis alba* in transition to flowering";*The Plant Journal* vol. 9(3) pp. 399–408 (1996).

\* cited by examiner

```
                         CCCAGATAGACATAAGAAAGAAAGAGAGAGAGAGATACTT
         TGGTCATTTCAGGGTTGTCGTTTCTCTCTCTTGTTCTTGAGATTTTGAAGAGAGAGAT
    1    ATGGGAAGAGGTAGGGTTCAGCTGAAGAGGATAGAGAACAAGATCAATAGGCAAGTTACT
    1     M  G  R  G  R  V  Q  L  K  R  I  E  N  K  I  N  R  Q  V  T

61    TTCTCAAAGAGAAGGTCTGGTTTGCTCAAGAAAGCTCATGAGATCTCTGTTCTCTGCGAT
   21     F  S  K  R  R  S  G  L  L  K  K  A  H  E  I  S  V  L  C  D

121    GCTGAGGTTGCTCTCATCGTCTTCTCTTCCAAAGGCAAACTCTTCGAATATTCCACCGAC
   41     A  E  V  A  L  I  V  F  S  S  K  G  K  L  F  E  Y  S  T  D

181    TCTTGCATGGAGAGGATACTTGAACGCTATGATCGCTATTTATATTCAGACAAACAACTT
   61     S  C  M  E  R  I  L  E  R  Y  D  R  Y  L  Y  S  D  K  Q  L

241    GTTGGCCGAGACGTTTCACAAAGTGAAAATTGGGTTCTAGAACATGCTAAGCTCAAGGCA
   81     V  G  R  D  V  S  Q  S  E  N  W  V  L  E  H  A  K  L  K  A

301    AGAGTTGAGGTACTTGAGAAGAACAAAAGGAATTTTATGGGGGAAGATCTTGATTCGTTG
  101     R  V  E  V  L  E  K  N  K  R  N  F  M  G  E  D  L  D  S  L

361    AGCTTGAAGGAGCTCCAAAGCTTGGAGCATCAGCTCGATGCAGCTATCAAGAGCATTAGG
  121     S  L  K  E  L  Q  S  L  E  H  Q  L  D  A  A  I  K  S  I  R

421    TCAAGAAAGAACCAAGCTATGTTCGAATCCATATCTGCGCTCCAGAAGAAGGATAAAGCC
  141     S  R  K  N  Q  A  M  F  E  S  I  S  A  L  Q  K  K  D  K  A

481    TTGCAAGATCACAACAATTCGCTTCTCAAAAAGATTAAGGAGAGGGAGAAGAAAACGGGT
  161     L  Q  D  H  N  N  S  L  L  K  K  I  K  E  R  E  K  K  T  G

541    CAGCAAGAAGGACAATTAGTCCAATGCTCCAACTCTTCTTCAGTTCTTCTGCCTCAATAC
  181     Q  Q  E  G  Q  L  V  Q  C  S  N  S  S  S  V  L  L  P  Q  Y

601    TGCGTAACCTCCTCCAGAGATGGCTTTGTGGAGAGAGTTGGGGGAGAGAACGGTGGTGCA
  201     C  V  T  S  S  R  D  G  F  V  E  R  V  G  G  E  N  G  G  A

661    TCGTCGTTGACGGAACCAAACTCTCTGCTTCCGGCTTGGATGTTACGTCCTACCACTACG
  221     S  S  L  T  E  P  N  S  L  L  P  A  W  M  L  R  P  T  T  T

721    AACGAGTAGAACTATCTCACTCTTTATAATATAATGATAATATAATTAATGTTTAATATT
  241     N  E  *

781    TTCATAACATTCAGCATTTTTTTGGTGACTTATACTCATTATTAATACCGATATGTTTTA
  841    GCTAGTCATATTATATGTATGATGGAACTCCGTTGTCGAGACGTATGTACGTAAGCTATC
  901    ATTAGATTCACTGCGTCTTAAGAACAAAGATTCATATCTTGGTAATGATTTCTCATGAAA
  961    TAn
```

FIG. 1

SEQUENCE LISTING

<160> NUMBER OF SEQ ID NOS: 4

<210> SEQ ID NO 1
<211> LENGTH: 1062
<212> TYPE: DNA
<213> ORGANISM: Arabidopsis sp.
<220> FEATURE:
<221> NAME/KEY: CDS
<222> LOCATION: (101)..(826)
<221> NAME/KEY: polyA_signal
<222> LOCATION: (1061)

<400> SEQUENCE: 1

```
cccagagaga cataagaaag aaagagagag agagatactt tggtcatttc agggttgtcg          60
tttctctctc ttgttcttga gattttgaag agagagagat atg gga aga ggt agg         115
                                             Met Gly Arg Gly Arg
                                              1               5 gtt cag ctg aag agg ata gag aac aag atc aat agg caa gtt act ttc         163
Val Gln Leu Lys Arg Ile Glu Asn Lys Ile Asn Arg Gln Val Thr Phe
             10                  15                  20 tca aag aga agg tct ggt ttg ctc aag aaa gct cat gag atc tct gtt         211
Ser Lys Arg Arg Ser Gly Leu Leu Lys Lys Ala His Glu Ile Ser Val
         25                  30                  35 ctc tgc gat gct gag gtt gct ctc atc gtc ttc tct tcc aaa ggc aaa         259
Leu Cys Asp Ala Glu Val Ala Leu Ile Val Phe Ser Ser Lys Gly Lys
     40                  45                  50 ctc ttc gaa tat tcc acc gac tct tgc atg gag agg ata ctt gaa cgc         307
Leu Phe Glu Tyr Ser Thr Asp Ser Cys Met Glu Arg Ile Leu Glu Arg
 55                  60                  65 tat gat cgc tat tta tat tca gac aaa caa ctt gtt ggc cga gac gtt         355
Tyr Asp Arg Tyr Leu Tyr Ser Asp Lys Gln Leu Val Gly Arg Asp Val
 70                  75                  80                  85 tca caa agt gaa aat tgg gtt cta gaa cat gct aag ctc aag gca aga         403
Ser Gln Ser Glu Asn Trp Val Leu Glu His Ala Lys Leu Lys Ala Arg
             90                  95                 100 gtt gag gta ctt gag aag aac aaa agg aat ttt atg ggg gaa gat ctt         451
Val Glu Val Leu Glu Lys Asn Lys Arg Asn Phe Met Gly Glu Asp Leu
        105                 110                 115 gat tcg ttg agc ttg aag gag ctc caa agc ttg gag cat cag ctc gat         499
Asp Ser Leu Ser Leu Lys Glu Leu Gln Ser Leu Glu His Gln Leu Asp
    120                 125                 130 gca gct atc aag agc att agg tca aga aag aac caa gct atg ttc gaa         547
Ala Ala Ile Lys Ser Ile Arg Ser Arg Lys Asn Gln Ala Met Phe Glu
135                 140                 145 tcc ata tct gcg ctc cag aag aag gat aaa gcc ttg caa gat cac aac         595
Ser Ile Ser Ala Leu Gln Lys Lys Asp Lys Ala Leu Gln Asp His Asn
150                 155                 160                 165 aat tcg ctt ctc aaa aag att aag gag agg gag aag aaa acg ggt cag         643
Asn Ser Leu Leu Lys Lys Ile Lys Glu Arg Glu Lys Lys Thr Gly Gln
            170                 175                 180 caa gaa gga caa tta gtc caa tgc tcc aac tct tct tca gtt ctt ctg         691
Gln Glu Gly Gln Leu Val Gln Cys Ser Asn Ser Ser Ser Val Leu Leu
        185                 190                 195 cct caa tac tgc gta acc tcc tcc aga gat ggc ttt gtg gag aga gtt         739
Pro Gln Tyr Cys Val Thr Ser Ser Arg Asp Gly Phe Val Glu Arg Val
        200                 205                 210 ggg gga gag aac ggt ggt gca tcg tcg ttg acg gaa cca aac tct ctg         787
Gly Gly Glu Asn Gly Gly Ala Ser Ser Leu Thr Glu Pro Asn Ser Leu
    215                 220                 225
```

```
ctt ccg gct tgg atg tta cgt cct acc act acg aac gag tagaactatc      836
Leu Pro Ala Trp Met Leu Arg Pro Thr Thr Thr Asn Glu
230                 235                 240 tcactctttta taatataatg ataatataat taatgtttaa tattttcata acattcagca   896 ttttttggt gacttatact cattattaat accgatatgt tttagctagt catattatat    956
gtatgatgga actccgttgt cgagacgtat gtacgtaagc tatcattaga ttcactgcgt   1016
cttaagaaca aagattcata tcttggtaat gatttctcat gaaata                  1062

<210> SEQ ID NO 2
<211> LENGTH: 242
<212> TYPE: PRT
<213> ORGANISM: Arabidopsis sp.

<400> SEQUENCE: 2

Met Gly Arg Gly Arg Val Gln Leu Lys Arg Ile Glu Asn Lys Ile Asn
1               5                   10                  15

Arg Gln Val Thr Phe Ser Lys Arg Arg Ser Gly Leu Leu Lys Lys Ala
                20                  25                  30

His Glu Ile Ser Val Leu Cys Asp Ala Glu Val Ala Leu Ile Val Phe
            35                  40                  45

Ser Ser Lys Gly Lys Leu Phe Glu Tyr Ser Thr Asp Ser Cys Met Glu
        50                  55                  60

Arg Ile Leu Glu Arg Tyr Asp Arg Tyr Leu Tyr Ser Asp Lys Gln Leu
65                  70                  75                  80

Val Gly Arg Asp Val Ser Gln Ser Glu Asn Trp Val Leu Glu His Ala
                85                  90                  95

Lys Leu Lys Ala Arg Val Glu Val Leu Glu Lys Asn Lys Arg Asn Phe
            100                 105                 110

Met Gly Glu Asp Leu Asp Ser Leu Ser Leu Lys Glu Leu Gln Ser Leu
        115                 120                 125

Glu His Gln Leu Asp Ala Ala Ile Lys Ser Ile Arg Ser Arg Lys Asn
    130                 135                 140

Gln Ala Met Phe Glu Ser Ile Ser Ala Leu Gln Lys Lys Asp Lys Ala
145                 150                 155                 160

Leu Gln Asp His Asn Asn Ser Leu Leu Lys Lys Ile Lys Glu Arg Glu
                165                 170                 175

Lys Lys Thr Gly Gln Gln Glu Gly Gln Leu Val Gln Cys Ser Asn Ser
            180                 185                 190

Ser Ser Val Leu Leu Pro Gln Tyr Cys Val Thr Ser Ser Arg Asp Gly
        195                 200                 205

Phe Val Glu Arg Val Gly Gly Gly Asn Gly Gly Ala Ser Ser Leu Thr
    210                 215                 220

Glu Pro Asn Ser Leu Leu Pro Ala Trp Met Leu Arg Pro Thr Thr Thr
225                 230                 235                 240

Asn Glu

<210> SEQ ID NO 3
<211> LENGTH: 27
<212> TYPE: DNA
<213> ORGANISM: Arabidopsis sp.

<400> SEQUENCE: 3
ccgtcgacga tgggaagagg tagggtt                                         27

<210> SEQ ID NO 4
```

```
<211> LENGTH: 20
<212> TYPE: DNA
<213> ORGANISM: Arabidopsis sp.

<400> SEQUENCE: 4
aatcattacc aagatatgaa                                              20
```

METHOD OF DECREASING SEED SIZE IN A PLANT

This application is a divisional application of U.S. patent application Ser. No. 09/105,652, now U.S. Pat. No. 6,229,068 filed Jun. 26, 1998, which application claims the benefit of priority of U.S. Provisional Application No. 60/051,030, filed Jun. 27, 1997, the entire contents of which is incorporated herein by reference.

This invention was made with government support under DCB9018749 and MCB9408042 awarded by the National Science Foundation. The government has certain rights in the invention.

BACKGROUND OF THE INVENTION

1. Field of the Invention

The present invention relates generally to plant molecular biology and genetic engineering and more specifically to the production of genetically modified seed plants from which enlarged or diminished seeds or fruits can be obtained.

2. Background Information

Seed and fruit production are multi-billion dollar commercial industries and primary sources of income for numerous states in the United States and for many countries around the world. Commercially valuable seeds include, for example, rapeseeds, cottonseeds and sunflower seeds, which are prized for the vegetable oil that can be pressed from the seed. The seeds of leguminous plants such as peas, beans and lentils also are commercially valuable as they are rich in proteins, with soybeans, for example, consisting of 40–45% protein and 18% fats and oils. In addition, coffee is a valuable crop made from the dried and roasted seeds of *Coffea arabica* plants, while chocolate is made from the cacao seed or "bean." Similarly, many fruits are commercially valuable, including, for example, corn, rice, wheat, barley and other cereals, nuts, legumes, tomatoes, and citrus fruits.

Unfortunately, seed and fruit production are both limited inherently, for example, due to the availability of suitable growing seasons and growing conditions, including the finite resource of arable land. In addition, seed and fruit production are limited by the yield obtained from a plant, which is a function, in part, of the average size of the seeds and fruits produced. As a consequence, methods for increasing seed or fruit production from a seed plant would help in combating the increased need for food, particularly as the world population continues to expand. Thus, a need exists for developing methods to increase the yield of seeds and fruits from cultivated plants. The present invention satisfies this need and provides related advantages as well.

SUMMARY OF THE INVENTION

The present invention provides a non-naturally occurring seed plant that is characterized by producing seeds of increased size due to ectopic expression of a nucleic acid molecule encoding an AGL8-related gene product. The AGL8-related gene product can have, for example, substantially the amino acid sequence of an AGL8 ortholog such as Arabidopsis AGL8 (SEQ ID NO:2).

In one embodiment, the invention provides a transgenic seed plant characterized by producing seeds of increased size due to ectopic expression of an exogenous nucleic acid molecule encoding an AGL8-related gene product. The nucleic acid molecule encoding the AGL8-related gene product can be operatively linked to an exogenous regulatory element such as a constitutive regulatory element or seed-selective regulatory element. The invention additionally provides a tissue, such as a seed, which is derived from a non-naturally occurring seed plant of the invention.

The invention further provides a method of producing a non-naturally occurring seed plant characterized by producing seeds of increased size. The method is practiced by ectopically expressing a nucleic acid molecule encoding an AGL8-related gene product in the seed plant, whereby seed size is increased due to ectopic expression of the nucleic acid molecule. In one embodiment, the method is practiced by introducing an exogenous nucleic acid molecule encoding an AGL8-related gene product into the seed plant.

Kits for generating a transgenic seed plant characterized by producing seeds of increased size also are provided herein. The kits of the invention include a nucleic acid molecule encoding an AGL8-related gene product and a seed-selective regulatory element. In a kit of the invention, the AGL8-related gene product can have, for example, substantially the amino acid sequence of an AGL8 ortholog. If desired, a kit for generating a transgenic seed plant characterized by producing seeds of increased size can include a plant expression vector containing a nucleic acid molecule encoding an AGL8-related gene product operatively linked to a seed-selective regulatory element.

The invention additionally provides a non-naturally occurring seed plant that is characterized by producing seeds of decreased size due to suppression of AGL8-related gene product expression. The AGL8-related gene product can have, for example, substantially the amino acid sequence of an AGL8 ortholog. In one embodiment, expression of the AGL8-related gene product is selectively suppressed in seed tissue. In addition, the invention provides a tissue, such as a seed, which is derived from a non-naturally occurring seed plant characterized by producing seeds of decreased size due to suppression of AGL8-related gene product expression.

Further provided herein is a non-naturally occurring seed plant that is characterized by producing fruit of increased size due to ectopic expression of a nucleic acid molecule encoding an AGL8-family gene product. The AGL8-family gene product can have substantially the amino acid sequence of an AGL8 ortholog, for example, the amino acid sequence of Arabidopsis AGL8 (SEQ ID NO:2).

In a related embodiment, the invention provides a transgenic seed plant that is characterized by producing fruit of increased size due to ectopic expression of an exogenous nucleic acid molecule encoding an AGL8-family gene product. The exogenous ectopically expressed nucleic acid molecule encoding an AGL8-family gene product can be operatively linked to an exogenous regulatory element, which can be, for example, a constitutive regulatory element or a valve-selective regulatory element.

A tissue derived from a non-naturally occurring seed plant that is characterized by producing fruit of increased size due to ectopic expression of a nucleic acid molecule encoding an AGL8-family gene product also is provided herein. The invention provides, for example, a fruit derived from a non-naturally occurring seed plant of the invention.

The invention also provides a method of generating a non-naturally occurring seed plant that is characterized by producing fruit of increased size. The method includes the step of ectopically expressing a nucleic acid molecule encoding an AGL8-family gene product in the seed plant, whereby fruit size is increased due to ectopic expression of the nucleic acid molecule. In one embodiment, the method includes the step of introducing an exogenous nucleic acid molecule encoding an AGL8-family gene product into the seed plant.

Further provided by the invention are kits for generating a transgenic seed plant characterized by producing fruit of increased size. The kits include a nucleic acid molecule encoding an AGL8-family gene product as well as a valve-selective regulatory element. The AGL8-family gene product can have, for example, substantially the amino acid sequence of an AGL8 ortholog. If desired, a kit of the invention can include a plant expression vector containing a nucleic acid molecule encoding an AGL8-family gene product operatively linked to a valve-selective regulatory element.

The invention further provides a non-naturally occurring seed plant that is characterized by producing fruit of decreased size, in which expression of an AGL8-family gene product is suppressed. In such a non-naturally occurring seed plant of the invention, an AGL8-family gene product can have, for example, substantially the amino acid sequence of an AGL8 ortholog. In one embodiment, expression of the AGL8-family gene product is selectively suppressed in valve tissue. Also provided herein is a tissue, such as a fruit, derived from a non-naturally occurring seed plant that is characterized by producing fruit of decreased size, in which expression of an AGL8-family gene product is suppressed.

BRIEF DESCRIPTION OF THE DRAWINGS

FIG. 1 shows the nucleotide (SEQ ID NO:1) and amino acid (SEQ ID NO:2) sequence of Arabidopsis AGL8.

DETAILED DESCRIPTION OF THE INVENTION

The present invention provides a non-naturally occurring seed plant that is characterized by producing seeds of increased size due to ectopic expression of a nucleic acid molecule encoding an AGL8-related gene product. The AGL8-related gene product can have, for example, substantially the amino acid sequence of an AGL8 ortholog such as Arabidopsis AGL8 (SEQ ID NO:2).

In one embodiment, the invention provides a transgenic seed plant characterized by producing seeds of increased size due to ectopic expression of an exogenous nucleic acid molecule encoding an AGL8-related gene product. The nucleic acid molecule encoding the AGL8-related gene product can be operatively linked to an exogenous regulatory element such as a constitutive regulatory element or seed-selective regulatory element.

The present invention is directed to the surprising discovery that the AGL8 transcription factor regulates seed size in a plant. As disclosed herein, AGL8 loss-of-function mutants were produced by Ds transposon insertion mutagenesis of Arabidopsis using the DsE enhancer trap transposable element and the Gus reporter gene (Sundaresan et al., *Genes Development* 9:1797–1810 (1995), which is incorporated by reference herein). Transposition events were selected and screened for reporter gene expression patterns and mutant phenotypes. The mutation affected cell differentiation of the valve, creating a zigzag pattern in the outer epidermis of the replum that fuses with the two carpel valves. Seeds in the mutant plants looked normal, except for a smaller size, and remained arranged in four rows as in the wild type. However, the seeds were highly compacted inside the fruit and the number of seeds in each fruit was reduced to about 75% the number of seeds produced by wild type plants.

As further disclosed herein, overexpression of AGL8 in Arabidopsis results in the production of seeds having an increased size as compared to the seeds produced by wild type Arabidopsis. As set forth in Example I, constitutive expression of AGL8 (SEQ ID NO:2) under control of a tandem cauliflower mosaic virus (CaMV) 35S promoter resulted in seeds having an abnormal size that was about three times the size of seeds produced by wild type plants. In view of the presence and expression of the AGL8 ortholog, SaMADS B, as well as the presence and expression of AGL orthologs in maize, the skilled artisan will recognize that an AGL8-related gene product, such as an ortholog of AGL8, can be used in the methods of the present invention, for example, to produce transgenic plants having the characteristics disclosed herein. Thus, the invention provides a non-naturally occurring seed plant, such as a transgenic seed plant, characterized by producing seeds of increased size due to ectopic expression of a nucleic acid molecule encoding an AGL8-related gene product.

As used herein, the term "non-naturally occurring," when used in reference to a seed plant, means a seed plant that has been genetically modified by man. A transgenic seed plant of the invention, for example, is a non-naturally occurring seed plant that contains an exogenous nucleic acid molecule, such as a nucleic acid molecule encoding an AGL8-related gene product and, therefore, has been genetically modified by man. In addition, a seed plant that contains, for example, a mutation in an endogenous AGL8-related gene product regulatory element or coding sequence as a result of calculated exposure to a mutagenic agent, such as a chemical mutagen, or an "insertional mutagen," such as a transposon, also is considered a non-naturally occurring seed plant, since it has been genetically modified by man. In contrast, a seed plant containing only spontaneous or naturally occurring mutations is not a "non-naturally occurring seed plant" as defined herein and, therefore, is not encompassed within the invention. One skilled in the art understands that, while a non-naturally occurring seed plant typically has a nucleotide sequence that is altered as compared to a naturally occurring seed plant, a non-naturally occurring seed plant also can be genetically modified by man without altering its nucleotide sequence, for example, by modifying its methylation pattern.

The term "ectopically," as used herein in reference to expression of a nucleic acid molecule, refers to an expression pattern that is distinct from the expression pattern in a wild type seed plant. Thus, one skilled in the art understands that ectopic expression of a nucleic acid molecule encoding an AGL8-related gene product can refer to expression in a cell type other than a cell type in which the nucleic acid molecule normally is expressed, or at a time other than a time at which the nucleic acid molecule normally is expressed, or at a level other than the level at which the nucleic acid molecule normally is expressed. In wild type Arabidopsis, for example, AGL8 expression is normally restricted during the later stages of floral development to the carpel valves and is not seen in the seeds. However, under control of a constitutive promoter such as the cauliflower mosaic virus 35S promoter, AGL8 is expressed in the seeds and, additionally, is expressed at higher than normal levels in valve tissue and, thus, is ectopically expressed.

The term "increased size," as used herein in reference to a seed produced by a non-naturally occurring seed plant of the invention, means a significantly greater seed volume or dry weight as compared to the volume or dry weight of seeds produced by a corresponding seed plant lacking an ectopically expressed nucleic acid molecule encoding an AGL8-related gene product such as a wild type seed plant. As disclosed herein in Example I, the seeds from a transgenic Arabidopsis plant ectopically expressing AGL8 (SEQ ID NO:2) produce seeds that have a greater volume and greater weight, exhibiting almost three times the dry weight of seeds produced from wild type Arabidopsis plants. An increased size can result, for example, from an increase in the number of cells in the seed.

It is recognized that there can be natural variation in the size of seeds produced by a particular seed plant species or variety. However, seeds of increased size produced by a seed plant using a method of the invention readily can be identified by sampling a population of the produced seeds and determining that the normal distribution of seed sizes is greater, on average, than the normal distribution of seeds produced by the corresponding seed plant variety or species lacking an ectopically expressed nucleic acid molecule encoding an AGL8-related gene product. Thus, production of non-naturally occurring seed plants of the invention provides a means to skew the normal distribution of seed sizes produced by a seed plant, such that the seed volumes or dry weights are, on average, at least about 5% greater, 10% greater, 20% greater, 30% greater, 50% greater, 75% greater, 100% greater, 200% greater, 300% greater, 400% greater or 500% greater than in the corresponding seed plant species that does not contain an ectopically expressed nucleic acid molecule encoding an AGL8-related gene product.

The present invention relates to the use of nucleic acid molecules encoding particular "AGAMOUS-LIKE" or "AGL" gene products. AGAMOUS (AG) is a floral organ identity gene, one of a related family of transcription factors that, in various combinations, specify the identity of the floral organs: the petals, sepals, stamens and carpels (Bowman et al., *Devel.* 112:1–20 (1991); Weigel and Meyerowitz, *Cell* 78:203–209 (1994); Yanofsky, *Annual Rev. Plant Physiol. Mol. Biol.* 46:167–188 (1995)). The AGAMOUS gene product is essential for specification of carpel and stamen identity (Bowman et al., *The Plant Cell* 1:37–52 (1989); Yanofsky et al., *Nature* 346:35–39 (1990)). Related genes have recently been identified and denoted "AGAMOUS-LIKE" or "AGL" genes (Ma et al., *Genes Devel.* 5:484–495 (1991); Mandel and Yanofsky, *The Plant Cell* 7:1763–1771 (1995), which is incorporated herein by reference).

AGL8, like AGAMOUS and other AGL genes, is characterized, in part, in that it is a plant MADS box gene. The plant MADS box genes generally encode proteins of about 260 amino acids including a highly conserved MADS domain of about 56 amino acids (Riechmann and Meyerowitz, *Biol. Chem.* 378:1079–1101 (1997), which is incorporated herein by reference). The MADS domain, which was first identified in the Arabidopsis AGAMOUS and *Antirrhinum majus* DEFICIENS genes, is conserved among transcription factors found in humans (serum response factor; SRF) and yeast (MCM1; Norman et al., *Cell* 55:989–1003 (1988); Passmore et al., *J. Mol. Biol.* 204:593–606 (1988), and is the most highly conserved region of the MADS domain proteins. The MADS domain is the major determinant of sequence specific DNA-binding activity and can also perform dimerization and other accessory functions (Huang et al., *The Plant Cell* 8:81–94 (1996)). The MADS domain frequently resides at the N-terminus, although some proteins contain additional residues N-terminal to the MADS domain.

The "intervening domain" or "I-domain," located immediately C-terminal to the MADS domain, is a weakly conserved domain having a variable length of approximately 30 amino acids (Purugganan et al., *Genetics* 140:345–356 (1995)). In some proteins, the I-domain plays a role in the formation of DNA-binding dimers. A third domain present in plant MADS domain proteins is a moderately conserved 70 amino acid region denoted the "keratin-like domain" or "K-domain." Named for its similarity to regions of the keratin molecule, the structure of the K-domain appears capable of forming amphipathic helices and may mediate protein-protein interactions (Ma et al., *Genes Devel.* 5:484–495 (1991)). The most variable domain, both in sequence and in length, is the carboxy-terminal or "C-domain" of the MADS domain proteins. Dispensable for DNA binding and protein dimerization in some MADS domain proteins, the function of this C-domain remains unknown.

Arabidopsis AGL8 is a 242 amino acid MADS box protein (SEQ ID NO:2; Mandel and Yanofsky, supra, 1995). The AGL8 MADS domain resides at amino acids 2 to 56 of SEQ ID NO:2. The K-domain of AGL8 resides at amino acids 92 to 158 of SEQ ID NO:2.

In wild-type Arabidopsis, AGL8 RNA accumulates in two distinct phases, the first occurring during inflorescence development in the stem and cauline leaves, and the second in the later stages of flower development (Mandel and Yanofsky, supra, 1995). In particular, AGL8 RNA is first detected in the inflorescence meristem as soon as the plant switches from vegetative to reproductive development. As the inflorescence stem elongates, AGL8 RNA accumulates in the inflorescence meristem and in the stem. Secondly, although AGL8 is not detected in the initial stages (1 and 2) of flower development, AGL8 expression resumes at approximately stage 3 in the center of the floral dome in the region corresponding to the fourth (carpel) whorl. AGL8 expression is excluded from all other primordia and the pedicel. The time of AGL8 expression in the fourth carpel whorl generally corresponds to the time at which the organ identity genes APETALA3, PISTILLATA AND AGAMOUS begin to be expressed (Yanofsky et al., *Nature* 346:35–39 (1990); Drews et al., *Cell* 65:991–1002 (1991); Jack et al., *Cell* 68:683–697 (1992); Goto and Meyerowitz, *Genes Devel.* 8:1548–1560 (1994)). At later stages, AGL8 expression becomes localized to the carpel walls, in the region that constitutes the valves of the ovary, and is absent from nearly all other cell types of the carpel. No AGL8 RNA expression is detected in the ovules, stigmatic tissues or the septum that divides the ovary. Thus, in nature, AGL8 expression during the later stages of floral development is restricted to the valves of the carpels and to the cells within the style.

As used herein, the term "AGL8-related gene product" means a gene product that has the same or similar function as Arabidopsis AGL8 such that, when ectopically expressed in a seed plant, normal development is altered such that seeds of increased size are produced. Arabidopsis AGL8 (SEQ ID NO:2) is an example of an AGL8-related gene product as defined herein. As disclosed in Example I, ectopic expression of Arabidopsis AGL8 (SEQ ID NO:2) under control of a tandem CaMV 35S promoter, in which the intrinsic promoter element has been duplicated, alters normal plant development such that seeds of about three times normal size are produced.

An AGL8-related gene product generally is characterized, in part, as containing a MADS domain. An AGL8-related gene product also generally is characterized by having an amino acid sequence that has at least about 50% amino acid identity with the amino acid sequence of Arabidopsis AGL8 (SEQ ID NO: 2). An AGL8-related gene product can have, for example, an amino acid sequence with greater than about 65% amino acid sequence identity with Arabidopsis AGL8

(SEQ ID NO:2), preferably greater than about 75% amino acid identity with Arabidopsis AGL8 (SEQ ID NO:2), more preferably greater than about 85% amino acid identity with Arabidopsis AGL8 (SEQ ID NO:2), and can be a sequence having greater than about 90%, 95% or 97% amino acid identity with Arabidopsis AGL8 (SEQ ID NO:2).

Preferably, an AGL8-related gene product is orthologous to the seed plant species in which it is ectopically expressed. A nucleic acid molecule encoding Arabidopsis AGL8 (SEQ ID NO:2), for example, can be ectopically expressed in an Arabidopsis plant to produce a non-naturally occurring Arabidopsis variety characterized by producing seeds of increased size. Similarly, a nucleic acid molecule encoding canola AGL8, for example, can be ectopically expressed in a canola plant to produce a non-naturally occurring canola variety characterized by producing canola seeds of increased size.

A nucleic acid molecule encoding an AGL8-related gene product also can be ectopically expressed in a heterologous seed plant to produce a non-naturally occurring seed plant characterized by producing seeds of increased size. AGL8-related genes are AGAMOUS-like genes, which are present in most, if not all, angiosperms. AGAMOUS, for example, has been conserved in tomato (TAG1) and maize (ZAG1), indicating that AGAMOUS-like gene products have been widely conserved throughout the plant kingdom (Pnueli et al., *The Plant Cell* 6:163–173 (1994); Schmidt et al., *The Plant Cell* 5:729–737 (1993)). AGL8-related gene products such as AGL8 orthologs also can be conserved and can function across species boundaries to produce seeds of increased size. Thus, ectopic expression of a nucleic acid molecule encoding Arabidopsis AGL8 (SEQ ID NO:2) in a heterologous seed plant within the Brassicaceae such as *Brassica napus* L. (rapeseed) or within the Fabaceae such as in Glycine (soybean), for example, can alter normal development and result in production of seeds of increased size. Furthermore, a nucleic acid molecule encoding Arabidopsis AGL8 (SEQ ID NO:2), for example, can be ectopically expressed in more distantly related heterologous seed plants, including dicotyledonous and monocotyledonous angiosperms and gymnosperms and, upon ectopic expression, can alter normal development such that seeds of increased size are produced by the heterologous seed plant.

As used herein, the term "AGL8-related gene product" encompasses an active segment of an AGL8-related gene product, which is a polypeptide portion of an AGL8-related gene product that, when ectopically expressed, alters normal development such that seeds of increased size are produced. An active segment can be, for example, an amino terminal, internal or carboxy terminal fragment of Arabidopsis AGL8 (SEQ ID NO:2) that, when ectopically expressed in a seed plant, alters normal development such that seeds of increased size are produced. An active segment of an AGL8-related gene product can include, for example, the MADS domain and can have the ability to bind DNA specifically. The skilled artisan will recognize that a nucleic acid molecule encoding an active segment of an AGL8-related gene product can be used to generate a seed plant of the invention characterized by producing seeds of increased size and in the related methods and kits of the invention described further below.

An active segment of an AGL8-related gene product can be identified using the methods described in Example I or using other routine methodology. Briefly, a seed plant such as Arabidopsis can be transformed with a nucleic acid molecule under control of a constitutive regulatory element such as a tandem CaMV 35S promoter. Phenotypic analysis of the seed plant reveals whether a seed plant ectopically expressing a particular polypeptide portion produces seeds of increased size. For analysis of a large number of polypeptide portions of an AGL8-related gene product, nucleic acid molecules encoding the polypeptide portions can be assayed in pools, and active pools subsequently subdivided to identify the active nucleic acid molecule.

In one embodiment, the invention provides a non-naturally occurring seed plant that is characterized by producing seeds of increased size due to ectopic expression of a nucleic acid molecule encoding an AGL8-related gene product having substantially the amino acid sequence of an AGL8 ortholog. As used herein, the term "AGL8 ortholog" means an ortholog of Arabidopsis AGL8 (SEQ ID NO:2) and refers to an AGL8-related gene product that, in a particular seed plant variety, has the highest percentage homology at the amino acid level to Arabidopsis AGL8 (SEQ ID NO:2). An AGL8 ortholog can be, for example, a Brassica AGL8 ortholog such as a *Brassica napus* L. AGL8 ortholog, or a Fabacea AGL8 ortholog such as a soybean, pea, lentil, or bean AGL8 ortholog. An AGL8 ortholog from the long-day plant *Sinapis alba*, designated SaMADS B, has been described (Menzel et al., *Plant J.* 9:399–408 (1996), which is incorporated herein by reference). Novel AGL8 ortholog cDNAs can be isolated from additional seed plant species using a nucleotide sequence as a probe and methods well known in the art of molecular biology (Glick and Thompson (eds.), *Methods in Plant Molecular Biology and Biotechnology*, Boca Raton, Fla.: CRC Press (1993); Sambrook et al. (eds.), *Molecular Cloning: A Laboratory Manual* (Second Edition), Plainview, N.Y.: Cold Spring Harbor Laboratory Press (1989), each of which is incorporated herein by reference).

As used herein, the term "substantially the amino acid sequence," when used in reference to an AGL8 ortholog, is intended to mean a polypeptide or polypeptide segment having an identical amino acid sequence, or a polypeptide or polypeptide segment having a similar, non-identical sequence that is considered by those skilled in the art to be a functionally equivalent amino acid sequence. For example, an AGL8-related gene product having substantially the amino acid sequence of Arabidopsis AGL8 can have an amino acid sequence identical to the sequence of Arabidopsis AGL8 (SEQ ID NO:2), or a similar, non-identical sequence that is functionally equivalent. In particular, a gene product that has "substantially the amino acid sequence" of an AGL8 ortholog can have one or more modifications such as amino acid additions, deletions or substitutions, including conservative or non-conservation substitutions, relative to the AGL8 amino acid sequence of SEQ ID NO:2, for example, provided that the modified polypeptide retains substantially the ability to alter normal development such that seeds of increased size are produced when the nucleic acid molecule is ectopically expressed in the seed plant. Comparison of sequences for substantial similarity can be performed between two sequences of any length and usually is performed with sequences between about 6 and 1200 residues, preferably between about 10 and 100 residues and more preferably between about 25 and 35 residues. Such comparisons for substantial similarity are performed using methodology routine in the art.

It is understood that minor modifications of primary amino acid sequence can result in an AGL8-related gene product that has substantially equivalent or enhanced function as compared to the AGL8 ortholog from which it was derived. Further, various molecules can be attached to an AGL8 ortholog or active segment thereof, for example, other polypeptides, antigenic or other peptide tags, carbohydrates, lipids, or chemical moieties. Such modifications are included within the term AGL8 ortholog as defined herein.

One or more point mutations can be introduced into a nucleic acid molecule encoding an AGL8 ortholog to yield a modified nucleic acid molecule using, for example, site-directed mutagenesis (see Wu (Ed.), *Meth. In Enzymol.* Vol. 217, San Diego: Academic Press (1993); Higuchi, "Recombinant PCR" in Innis et al. (Ed.), *PCR Protocols,* San Diego: Academic Press, Inc. (1990), each of which is incorporated herein by reference). Such mutagenesis can be used to introduce a specific, desired amino acid insertion, deletion or substitution; alternatively, a nucleic acid sequence can be synthesized having random nucleotides at one or more predetermined positions to generate random amino acid substitutions. Scanning mutagenesis also can be useful in generating a modified nucleic acid molecule encoding substantially the amino acid sequence of an AGL8 ortholog.

Modified nucleic aci d molecules can be routinely assayed for the ability to alter normal plant development such that seeds of incre ased size are produced. In the same manner as described in Example I, a nucleic acid molecule encoding substantially the amino acid sequence of an AGL8 ortholog can be ectopically expressed, for example, using a constitutive regulatory element such as th e CaMV 35S promoter or using a tissue-specific regulatory element such as a seed-selective regulatory element as described further below. If such ectopic expression results in a seed plant in which seeds of increased size are produced, the modified polypeptide or segment is an "AGL8 ortholog" as defined herein.

A non-naturally occurring seed plant of the invention that is characterized by producing seeds of increased size can be one of a variety of seed plant species, including a monocotyledonous or dicotyledonous angiosperm or a gymnosperm. A useful seed plant of the invention can be, for example, a member of the Brassicaceae, such as rapeseed, or a member of the Fabaceae, such as a soybean, pea, lentil or bean plant.

As used herein, the term "seed plant" means an angiosperm or gymnosperm. An angiosperm is a seed-bearing plant whose seeds are borne in a mature ovary (fruit). An angiosperm commonly is recognized as a flowering plant. Angiosperms are divided into two broad classes based on the number of cotyledons, which are seed leaves that generally store or absorb food. Thus, a monocotyledonous angiosperm is an angiosperm having a single cotyledon, whereas a dicotyledonous angiosperm is an angiosperm having two cotyledons. A variety of angiosperms are known including, for example, oilseed plants, leguminous plants, fruit-bearing plants, ornamental flowers, cereal plants and hardwood trees, which general classes are not necessarily exclusive. The skilled artisan will recognize that the methods of the invention can be practiced using these or other angiosperms, as desired. The invention also can be practiced with a gymnosperm, which is a seed-bearing plant having seeds not enclosed in an ovary.

In one embodiment, the invention provides a non-naturally occurring seed plant that is characterized by producing seeds of increased size due to ectopic expression of a nucleic acid molecule encoding an AGL8-related gene product, where the seed plant is a member of the Brassicaceae. The Brassicaceae, commonly known as the "Brassicas," are a diverse group of crop plants including the particularly valuable oilseed plant canola (see, for example, Williams and Hill, *Science* 232:1385–1389 (1986), which is incorporated herein by reference). The Brassicaceae include six major species, each containing a range of plant forms: *Brassica napus, Brassica oleracea, Brassica campestris (Brassica rapa), Brassica juncea;* and *Brassica carinata.* The skilled artisan understands that any member of the Brassicaceae can be modified as disclosed herein to produce a non-naturally occurring Brassica seed plant characterized by producing seeds of increased size.

The invention also provides a non-naturally occurring seed plant that is characterized by producing seeds of increased size due to ectopic expression of a nucleic acid molecule encoding an AGL8-related gene product, where the seed plant is a member of the Fabaceae. The Fabaceae, which are commonly known as members of the pea family, are seed plants that produce a characteristic dry dehiscent fruit known as a legume. A member of the Fabaceae, for example, a plant that produces a grain legume such as soybean (glycine), pea, chickpea, moth bean, broad bean, kidney bean, lima bean, lentil, cowpea, dry bean or peanut, can be modified as described herein to generate a non-naturally occurring variety characterized by producing seeds of increased size.

A non-naturally occurring seed plant of the invention characterized by producing seeds of increased size also can be an oilseed plant, such as a member of the plant genus Cuphea (family Lythraceae). A Cuphea seed plant is particularly valuable since Cuphea oilseeds contain industrially and nutritionally important medium-chain fatty acids, especially lauric acid, which is currently supplied only by coconut and palm kernel oils. Other oilseed plants that can be modified as disclosed herein to produce seeds of increased size include, for example, the cultivated sunflower (*Helianthus annuus* L.) and cotton plants such as Gossypium that are cultivated for their cottonseeds.

A non-naturally occurring seed plant of the invention characterized by producing seeds of increased size also can be, for example, a coffee plant (*Coffea arabica*) or a cacao plant (*Theobroma cacao*). The skilled artisan will realize that the invention can be practiced with these or other seed plant species, as desired, to increase the yield of commercially valuable seeds.

The invention also provides a transgenic seed plant that is characterized by producing seeds of increased size due to ectopic expression of an exogenous nucleic acid molecule encoding an AGL8-related gene product. In a transgenic seed plant of the invention, the ectopically expressed exogenous nucleic acid molecule encoding an AGL8-related gene product can be operatively linked to an exogenous regulatory element. In one embodiment, the invention provides a transgenic seed plant characterized by producing seeds of increased size having an ectopically expressed exogenous nucleic acid molecule encoding an AGL8-related gene product that is operatively linked to a constitutive regulatory element. The invention provides, for example, a transgenic seed plant that is characterized by producing seeds of increased size due to ectopic expression of an exogenous nucleic acid molecule encoding substantially the amino acid sequence of an AGL8 ortholog operatively linked to a cauliflower mosaic virus 35S promoter. In another embodiment, the invention provides a transgenic seed plant that is characterized by producing seeds of increased size due to ectopic expression of an exogenous nucleic acid molecule encoding an AGL8-related gene product operatively linked to a seed-selective regulatory element.

As used herein, the term "transgenic" refers to a seed plant that contains an exogenous nucleic acid molecule, which can be derived from the same seed plant species or from a heterologous seed plant species.

The term "exogenous," as used herein in reference to a nucleic acid molecule and a transgenic seed plant, means a nucleic acid molecule originating from outside the seed plant. An exogenous nucleic acid molecule can have a naturally occurring or non-naturally occurring nucleotide sequence. One skilled in the art understands that an exogenous nucleic acid molecule can be a heterologous nucleic acid molecule derived from a different seed plant species than the seed plant into which the nucleic acid molecule is introduced or can be a nucleic acid molecule derived from the same seed plant species as the seed plant into which it is introduced.

The term "operatively linked," as used in reference to a regulatory element and a nucleic acid molecule, such as a nucleic acid molecule encoding an AGL8-related gene product, means that the regulatory element confers regulated expression upon the operatively linked nucleic acid molecule. Thus, the term "operatively linked," as used in reference to an exogenous regulatory element such as a constitutive regulatory element and a nucleic acid molecule encoding an AGL8-related gene product, means that the constitutive regulatory element is linked to the nucleic acid molecule encoding an AGL8-related gene product such that the expression pattern of the constitutive regulatory element is conferred upon the nucleic acid molecule encoding the AGL8-related gene product. It is recognized that a regulatory element and a nucleic acid molecule that are operatively linked have, at a minimum, all elements essential for transcription, including, for example, a TATA box.

As used herein, the term "constitutive regulatory element" means a regulatory element that confers a level of expression upon an operatively linked nucleic molecule that is relatively independent of the cell or tissue type in which the constitutive regulatory element is expressed. A constitutive regulatory element that is expressed in a seed plant generally is widely expressed in a large number of cell and tissue types.

A variety of constitutive regulatory elements useful for ectopic expression in a transgenic seed plant of the invention are well known in the art. The cauliflower mosaic virus 35S (CaMV 35S) promoter, for example, is a well-characterized constitutive regulatory element that produces a high level of expression in all plant tissues (Odell et al., *Nature* 313:810–812 (1985)). The CaMV 35S promoter can be particularly useful due to its activity in numerous diverse seed plant species (Benfey and Chua, *Science* 250:959–966 (1990); Futterer et al., *Physiol. Plant* 79:154 (1990); Odell et al., supra, 1985). A tandem 35S promoter, in which the intrinsic promoter element has been duplicated, confers higher expression levels in comparison to the unmodified 35S promoter (Kay et al., *Science* 236:1299 (1987)). Other constitutive regulatory elements useful for ectopically expressing a nucleic acid molecule encoding an AGL8-related gene product in a transgenic seed plant of the invention include, for example, the cauliflower mosaic virus 19S promoter; the Figwort mosaic virus promoter; and the nopaline synthase (nos) gene promoter (Singer et al., *Plant Mol. Biol.* 14:433 (1990); An, *Plant Physiol.* 81:86 (1986)).

Additional constitutive regulatory elements including those for efficient ectopic expression in monocots also are known in the art, for example, the pEmu promoter and promoters based on the rice Actin-1 5' region (Last et al., *Theor. Appl. Genet.* 81:581 (1991); Mcelroy et al., *Mol. Gen. Genet.* 231:150 (1991); Mcelroy et al., *Plant Cell* 2:163 (1990)). Chimeric regulatory elements, which combine elements from different genes, also can be useful for ectopically expressing a nucleic acid molecule encoding an AGL8-related gene product (Comai et al., *Plant Mol. Biol.* 15:373 (1990)). One skilled in the art understands that a particular constitutive regulatory element is chosen based, in part, on the seed plant species in which a nucleic acid molecule encoding an AGL8-related gene product is to be ectopically expressed and on the desired level of expression.

As used herein, the term "seed-selective regulatory element" refers to a nucleotide sequence that, when operatively linked to a nucleic acid molecule, confers selective expression upon the operatively linked nucleic acid molecule in a limited number of plant tissues, including one or more seed tissues. A seed-selective regulatory element can confer specific expression exclusively in seed tissues, or can confer selective expression in a limited number of plant tissues including one or more seed tissues.

Seed-selective regulatory elements can be derived, for example, from a variety of genes that are selectively expressed in the seed tissue of a seed plant, for example, in the seed coat, endosperm or seed embryo (see, for example, West and Harada, *Plant Cell* 5:1361–1369 (1993), and Goldberg et al., *Science* 266:506–614 (1994), each of which is incorporated herein by reference). For example, the AGL15 gene is selectively expressed in the seed as described in Heck et al., *Plant Cell* 7:1271–1282 (1995) and Perry et al., *Plant Cell* 8:1977–1989 (1996), each of which is incorporated herein by reference. Thus, an AGL15 promoter or an active fragment thereof can be a seed-selective regulatory element as defined herein. The 1511 seed coat gene also is selectively expressed in the seed coat and, therefore, a 1511 promoter or active fragment thereof, such as a fragment of the genomic sequence available as GenBank accession number AC 000375, can be a seed-selective regulatory element. A promoter or active fragment of a zein storage protein gene such as a gene encoding the 22 KDa protein, which is selectively expressed in seed endosperm, also can be a useful seed-selective regulatory element (Burr et al., *J. Mol. Biol.* 154:33–49 (1982); Aukerman et al., *Genes & Devel.* 5:310–320 (1991); and Schmidt et al., *Proc. Natl. Acad. Sci., USA* 87:46–50 (1990), each of which is incorporated herein by reference). Additional genes such as SHOOTMERISTEMLESS are known to be selectively expressed in seed embryo; a SHOOTMERISTEMLESS promoter or an active fragment thereof, such as a fragment of the sequence available as GenBank accession number AC 003113, also can be a seed-selective regulatory element useful in practicing the invention (Long et al., *Nature* 379:66–69 (1996), which is incorporated herein by reference). The skilled artisan understands that a regulatory element of any such gene selectively expressed in seed tissue can be a seed-selective regulatory element as defined herein, provided that the element confers selective expression in one or more seed tissues upon an operatively linked nucleic acid molecule.

Additional seed-selective regulatory elements can be identified and isolated using routine methodology. Differential screening strategies using, for example, RNA prepared from the seed coat, endosperm or seed embryo and RNA prepared from non-seed tissue, such as root or leaf tissue, can be used to isolate cDNAs selectively expressed in the seed; subsequently, the corresponding genes are isolated using the cDNA sequence as a probe.

Enhancer trap or gene trap strategies also can be used to identify and isolate a seed-selective regulatory element of the invention (Sundaresan et al., supra, 1995; Springer et al., Science 268:877–880 (1995); Koncz et al., Proc. Natl. Acad. Sci. USA 86:8467–8471 (1989); Kertbundit et al., Proc. Natl. Acad. Sci. USA 88:5212–5216 (1991); Topping et al., Development 112:1009–1019 (1991), each of which is incorporated herein by reference). Enhancer trap elements include a reporter gene such as GUS with a weak or minimal promoter, while gene trap elements lack a promoter sequence, relying on transcription from a flanking chromosomal gene for reporter gene expression. Transposable elements included in the constructs mediate fusions to endogenous loci; constructs selectively expressed in seed tissue, such as in the seed coat, endosperm or seed embryo, are identified by their pattern of expression. With the inserted element as a tag, the flanking seed-selective regulatory element is cloned using, for example, inverse polymerase chain reaction methodology (see, for example, Aarts et al., Nature 363:715–717 (1993); see, also, Ochman et al., "Amplification of Flanking Sequences by Inverse PCR," in Innis et al., supra, 1990). The Ac/Ds transposition system of Sundaresan et al., supra, 1995, can be particularly useful in identifying and isolating a seed-selective regulatory element of the invention.

Seed-selective regulatory elements also can be isolated by inserting a library of random genomic DNA fragments in front of a promoterless reporter gene and screening transgenic seed plants transformed with the library for seed-selective reporter gene expression. The promoterless vector pROA97, which contains the npt gene and the GUS gene each under the control of the minimal 35S promoter, can be useful for such screening. The genomic library can be, for example, Sau3A fragments of Arabidopsis thaliana genomic DNA or genomic DNA from, for example, another Brassicaceae, Fabaceae or oilseed plant of interest (Ott et al., Mol. Gen. Genet. 223:169–179 (1990); Claes et al., The Plant Journal 1:15–26 (1991), each of which is incorporated herein by reference).

Seed-selective expression of a regulatory element of the invention can be demonstrated or confirmed by routine techniques, for example, using a reporter gene and in situ expression analysis. The GUS and firefly luciferase reporters are particularly useful for in situ localization of plant gene expression (Jefferson et al., EMBO J. 6:3901 (1987); Ow et al., Science 334:856 (1986), each of which is incorporated herein by reference); promoterless vectors containing the GUS expression cassette are commercially available, for example, from Clontech (Palo Alto, Calif.). To identify a seed-selective regulatory element, the desired nucleic acid sequence is generated using enzymatic or PCR-based methodology (Glick and Thompson, supra, 1993; Innis et al., supra, 1990); the resulting segments are fused to a reporter gene such as GUS and analyzed as described above.

An exogenous regulatory element useful in a transgenic seed plant of the invention also can be an inducible regulatory element, which is a regulatory element that confers conditional expression upon an operatively linked nucleic acid molecule, where expression of the operatively linked nucleic acid molecule is increased in the presence of a particular inducing agent or stimulus as compared to expression of the nucleic acid molecule in the absence of the inducing agent or stimulus. Particularly useful inducible regulatory elements include copper-inducible regulatory elements (Mett et al., Proc. Natl. Acad. Sci. USA 90:4567–4571 (1993); Furst et al., Cell 55:705–717 (1988)); tetracycline and chlor-tetracycline-inducible regulatory elements (Gatz et al., Plant J. 2:397–404 (1992); Röder et al., Mol. Gen. Genet. 243:32–38 (1994); Gatz, Meth. Cell Biol. 50:411–424 (1995)); ecdysone inducible regulatory elements (Christopherson et al., Proc. Natl. Acad. Sci. USA 89:6314–6318 (1992); Kreutzweiser et al., Ecotoxicol. Environ. Safety 28:14–24 (1994)); heat shock inducible regulatory elements (Takahashi et al., Plant Physiol. 99:383–390 (1992); Yabe et al., Plant Cell Physiol. 35:1207–1219 (1994); Ueda et al., Mol. Gen. Genet. 250:533–539 (1996)); and lac operon elements, which are used in combination with a constitutively expressed lac repressor to confer, for example, IPTG-inducible expression (Wilde et al., EMBO J. 11:1251–1259 (1992)).

An inducible regulatory element useful in the transgenic seed plants of the invention also can be, for example, a nitrate-inducible promoter derived from the spinach nitrite reductase gene (Back et al., Plant Mol. Biol. 17:9 (1991)) or a light-inducible promoter, such as that associated with the small subunit of RuBP carboxylase or the LHCP gene families (Feinbaum et al., Mol. Gen. Genet. 226:449 (1991); Lam and Chua, Science 248:471 (1990)). Additional inducible regulatory elements include salicylic acid inducible regulatory elements (Uknes et al., Plant Cell 5:159–169 (1993); Bi et al., Plant J. 8:235–245 (1995)); plant hormone-inducible regulatory elements (Yamaguchi-Shinozaki et al., Plant Mol. Biol. 15:905 (1990); Kares et al., Plant Mol. Biol. 15:225 (1990)); and human hormone-inducible regulatory elements such as the human glucocorticoid response element (Schena et al., Proc. Natl. Acad. Sci. USA 88:10421 (1991)).

The present invention further provides a tissue derived from a non-naturally occurring seed plant characterized by producing seeds of increased size due to ectopic expression of a nucleic acid molecule encoding an AGL8-related gene product. A particularly valuable tissue can be, for example, a seed.

As used herein, the term "tissue" means an aggregate of seed plant cells and intercellular material organized into a structural and functional unit. A tissue of the invention can be, for example, a seed, a fruit, a leaf, a root or part thereof. A particularly useful tissue of the invention is a seed or a fruit. A particularly useful tissue of the invention also can be a tissue that can be vegetatively or non-vegetatively propagated such that the seed plant from which the tissue was derived is reproduced.

As used herein, the term "seed" means a structure formed by the maturation of the ovule of a seed plant following fertilization. Such seeds can be readily harvested from a non-naturally occurring seed plant of the invention.

It should be recognized that a non-naturally occurring seed plant of the invention, which contains an ectopically expressed nucleic acid molecule encoding an AGL8-related gene product, also can contain one or more additional modifications, including naturally and non-naturally occurring mutations that can, for example, modulate the increase in seed size.

The invention further provides a method of producing a non-naturally occurring seed plant characterized by producing seeds of increased size. The method is practiced by ectopically expressing a nucleic acid molecule encoding an AGL8-related gene product in the seed plant, whereby seed size is increased due to ectopic expression of the nucleic acid molecule. In one embodiment, the method is practiced by introducing an exogenous nucleic acid molecule encoding an AGL8-related gene product into the seed plant.

As discussed above, the term "ectopically" refers to expression of a nucleic acid molecule encoding an AGL8-related gene product in a cell type other than a cell type in which the nucleic acid molecule is normally expressed, at a time other than a time at which the nucleic acid molecule is normally expressed or at an expression level other than the level at which the nucleic acid molecule normally is expressed.

Actual ectopic expression of an AGL8-related gene product is dependent on various factors. The ectopic expression can be widespread expression throughout most or all plant tissues or can be expression restricted to a small number of plant tissues, and can be achieved by a variety of routine techniques. Mutagenesis, including seed or pollen mutagenesis, can be used to generate a non-naturally occurring seed plant, in which a nucleic acid molecule encoding an AGL8-related gene product is ectopically expressed. Ethylmethane sulfonate (EMS) mutagenesis, transposon mediated mutagenesis or T-DNA mediated mutagenesis also can be useful in ectopically expressing an AGL8-related gene product to produce a seed plant that produces seeds of increased size (see, generally, Glick and Thompson, supra, 1993). While not wishing to be bound by any particular mechanism, ectopic expression in a mutagenized plant can result from inactivation of one or more negative regulators of AGL8, for example, from the combined inactivation of AGL1 and AGL5.

Ectopic expression of an AGL8-related gene product also can be achieved by expression of a nucleic acid molecule encoding an AGL8-related gene product from a heterologous regulatory element or from a modified variant of its own promoter. Heterologous regulatory elements include constitutive regulatory elements, which result in expression of the AGL8-related gene product in the seed as well as in a variety of other cell types, and seed-selective regulatory elements, which produce selective expression of an AGL8-related gene product in a limited number of plant tissues, including one or more seed tissues.

Ectopic expression of a nucleic acid molecule encoding an AGL8-related gene product can be achieved using an endogenous or exogenous nucleic acid molecule encoding an AGL8-related gene product. A recombinant exogenous nucleic acid molecule can contain a heterologous regulatory element that is operatively linked to a nucleic acid sequence encoding an AGL8-related gene product. Methods for producing the desired recombinant nucleic acid molecule under control of a heterologous regulatory element and for producing a non-naturally occurring seed plant of the invention are well known in the art (see, generally, Sambrook et al., supra, 1989; Glick and Thompson, supra, 1993).

An exogenous nucleic acid molecule can be introduced into a seed plant for ectopic expression using a variety of transformation methodologies including Agrobacterium-mediated transformation and direct gene transfer methods such as electroporation and microprojectile-mediated transformation (see, generally, Wang et al. (eds), *Transformation of Plants and Soil Microorganisms,* Cambridge, UK: University Press (1995), which is incorporated herein by reference). Transformation methods based upon the soil bacterium *Agrobacterium tumefaciens* are particularly useful-for introducing an exogenous nucleic acid molecule into a seed plant. The wild type form of Agrobacterium contains a Ti (tumor-inducing) plasmid that directs production of tumorigenic crown gall growth on host plants. Transfer of the tumor-inducing T-DNA region of the Ti plasmid to a plant genome requires the Ti plasmid-encoded virulence genes as well as T-DNA borders, which are a set of direct DNA repeats that delineate the region to be transferred. An Agrobacterium-based vector is a modified form of a Ti plasmid, in which the tumor inducing functions are replaced by the nucleic acid sequence of interest to be introduced into the plant host.

Agrobacterium-mediated transformation generally employs cointegrate vectors or, preferably, binary vector systems, in which the components of the Ti plasmid are divided between a helper vector, which resides permanently in the Agrobacterium host and carries the virulence genes, and a shuttle vector, which contains the gene of interest bounded by T-DNA sequences. A variety of binary vectors are well known in the art and are commercially available, for example, from Clontech (Palo Alto, Calif.). Methods of coculturing Agrobacterium with cultured plant cells or wounded tissue such as leaf tissue, root explants, hypocotyledons, stem pieces or tubers, for example, also are well known in the art (Glick and Thompson, supra, 1993). Wounded cells within the plant tissue that have been infected by Agrobacterium can develop organs de novo when cultured under the appropriate conditions; the resulting transgenic shoots eventually give rise to transgenic plants that ectopically express a nucleic acid molecule encoding an AGL8-related gene product. Agrobacterium also can be used for transformation of whole seed plants as described in Bechtold et al., *C.R. Acad. Sci. Paris, Life Sci.* 316:1194–1199 (1993), which is incorporated herein by reference). Agrobacterium-mediated transformation is useful for producing a variety of transgenic seed plants (Wang et al., supra, 1995) including transgenic plants of the Brassicaceae family, such as rapeseed and flax, and transgenic plants of the Fabaceae family such as soybean, pea, lentil and bean.

Microprojectile-mediated transformation also can be used to produce a transgenic seed plant that ectopically expresses an AGL8-related gene product. This method, first described by Klein et al. (*Nature* 327:70–73 (1987), which is incorporated herein by reference), relies on microprojectiles such as gold or tungsten that are coated with the desired nucleic acid molecule by precipitation with calcium chloride, spermidine or PEG. The microprojectile particles are accelerated at high speed into an angiosperm tissue using a device such as the BIOLISTIC PD-1000 (Biorad; Hercules Calif.).

Microprojectile-mediated delivery or "particle bombardment" is especially useful to transform seed plants that are difficult to transform or regenerate using other methods. Microprojectile-mediated transformation has been used, for example, to generate a variety of transgenic plant species, including cotton, tobacco, corn, hybrid poplar and papaya (see Glick and hompson, supra, 1993) as well as cereal crops such as heat, oat, barley, sorghum and rice (Duan et al., *Nature Biotech.* 14:494–498 (1996); Shimamoto, *Curr. Opin. Biotech.* 5:158–162 (1994), each of which is incorporated herein by reference). In view of the above, the skilled artisan will recognize that Agrobacterium-mediated or microprojectile-mediated transformation, as disclosed herein, or other methods known in the art can be used to produce a transgenic seed plant of the invention.

As disclosed herein, an agl8 mutant plant has smaller seeds as compared to the seeds produced by a wild type Arabidopsis plant. Thus, in addition to the embodiment described above, the invention provides a non-naturally occurring seed plant that is characterized by producing seeds of decreased size due to suppression of AGL8-related gene product expression. The AGL8-related gene product can have, for example, substantially the amino acid sequence of an AGL8 ortholog. In one embodiment, expression of the AGL8-related gene product is selectively suppressed in seed tissue. In addition, the invention provides a tissue, such as a seed, which is derived from a non-naturally occurring seed plant characterized by producing seeds of decreased size due to suppression of AGL8-related gene product expression.

Particularly valuable seed plant species that can be modified as disclosed herein to produce seeds of decreased size include, for example, plants that produce cottonseed grown for cloth production, cucumber plants, tomato plants, citrus trees and watermelon plants.

The term "decreased size," as used herein in reference to a seed produced by a non-naturally occurring seed plant of the invention, means a significantly reduced seed volume or dry weight as compared to the volume or dry weight of seeds produced by a corresponding seed plant in which expression of an AGL8-related gene product is not suppressed, for example, a wild type seed plant. Seeds of decreased size can have volumes or dry weights that are, on average, less than about 9/10, 8/10, 7/10, 5/10, 3/10, 2/10 or 1/10 the volume or dry weight of the seeds produced by a corresponding wil type seed plant.

The term "suppressed," as used herein in reference to expression of an AGL8-related gene product, means that the amount of functional AGL8-related gene product is reduced in a seed plant in comparison with the amount of functional AGL8-related gene product in the corresponding wild type seed plant. Thus, the term "suppressed," as used herein, encompasses the absence of AGL8-related gene product in a seed plant, as well as AGL8-related gene product expression that is present but reduced as compared to the level of this gene product in a wild type seed plant. Furthermore, the term suppressed refers to AGL8-related gene product expression that is reduced throughout the entire domain of AGL8-related gene product expression, or to expression that is reduced in some part of the AGL8-related gene product expression domain, provided that the resulting seed plant is characterized by producing seeds of decreased size.

As used herein, the term "suppressed" also encompasses an amount of AGL8-related gene product that is equivalent to the amount of AGL8-related gene product in a corresponding wild type seed plant, but where the AGL8-related gene product has a reduced level of activity. As discussed above, an AGL8-related gene product can contain a conserved MADS domain; thus, for example, point mutations or gross deletions within the MADS domain that reduce the DNA-binding activity of an AGL8-related gene product can reduce or destroy its activity and, therefore, "suppress" AGL8-related gene product expression as defined herein. One skilled in the art will recognize that, in one embodiment, AGL8-related gene product expression is essentially absent in the seed plant or the AGL8-related gene product is essentially non-functional.

A variety of methodologies can be used to suppress AGL8-related gene product expression in a seed plant. Suppression can be achieved by directly modifying the genomic locus of an AGL8-related gene product, for example, by modifying the regulatory sequence of an AGL8 ortholog such that transcription or translation from the AGL8 ortholog locus is reduced, or by modifying the coding sequence of an AGL8 ortholog such that a non-functional AGL8-related gene product is produced. Suppression of AGL8-related gene product expression in a seed plant also can be achieved indirectly, for example, by modifying the expression or activity of a protein that regulates expression of the AGL8-related gene product. Methodologies for effecting suppression of an AGL8-related gene product expression in a seed plant include, for example, homologous recombination, chemical and transposon-mediated mutagenesis, cosuppression and antisense-based techniques and dominant negative methodologies.

Homologous recombination of AGL1 or AGL5 can be used to suppress AGL8-related gene product expression in a seed plant. The use of homologous recombination in plants is described, for example, in Kempin et al., *Nature* 389:802–803 (1997), which is incorporated herein by reference.

Suppression of AGL8-related gene product expression also can be achieved by producing a loss-of-function mutation using transposon-mediated insertional mutagenesis with Ds transposons or Stm transposons (see, for example, Sundaresan et al., *Genes Devel.* 9:1797–1810 (1995), which is incorporated herein by reference). Insertion of a transposon into an AGL8-related gene product target gene can be identified, for example, by restriction mapping, which can identify the presence of an insertion in the gene promoter or in the coding region, such that expression of functional gene product is suppressed. Insertion of a transposon also can be identified by detecting an absence of the mRNA encoded by the target gene or by the detecting the absence of the gene product. Suppression of AGL8-related gene product expression also can be achieved by producing a loss-of-function mutation using T-DNA-mediated insertional mutagenesis (see, for example, Krysan et al., *Proc. Natl. Acad. Sci., USA* 93:8145–8150 (1996)).

Suppression of AGL8-related gene product expression in a seed plant also can be achieved using cosuppression, which is a well known methodology that relies on expression of a nucleic acid molecule in the sense orientation to produce coordinate silencing of the introduced nucleic acid molecule and the homologous endogenous gene (see, for example, Flavell, *Proc. Natl. Acad. Sci., USA* 91:3490–3496 (1994); Kooter and Mol, *Current Opin. Biol.* 4:166–171 (1993), each of which is incorporated herein by reference). Cosuppression is induced most strongly by a large number of transgene copies or by overexpression of transgene RNA and can be enhanced by modification of the transgene such that it fails to be translated.

Antisense nucleic acid molecules encoding an AGL8-related gene product, or fragments thereof, also can be used to suppress expression of an AGL8-related gene product in a seed plant. Antisense nucleic acid molecules reduce mRNA translation or increase mRNA degradation, thereby suppressing gene expression (see, for example, Kooter and Mol, supra, 1993; Pnueli et al., *The Plant Cell* Vol. 6, 175–186 (1994), which is incorporated herein by reference).

To produce a non-naturally occurring seed plant of the invention, in which AGL8-related gene product expression is suppressed, the one or more sense or antisense nucleic acid molecules can be expressed under control of a strong regulatory element such as a constitutive regulatory element or a seed-selective regulatory element described hereinabove.

The skilled artisan will recognize that effective suppression of endogenous AGL8-related gene product expression depends upon the one or more introduced nucleic acid molecules having a high percentage of homology with the corresponding endogenous gene loci. A nucleic acid molecule encoding Arabidopsis AGL8 (SEQ ID NO:2) is provided herein. A nucleic acid molecule encoding Arabidopsis AGL8 can be useful in the methods of the invention or for isolating an orthologous AGL8 sequence.

The homology requirement for effective suppression using homologous recombination, cosuppression or antisense methodology can be determined empirically. In general, a minimum of about 80–90% nucleic acid sequence identity is preferred for effective suppression of AGL8-related gene product expression. Thus, a nucleic acid molecule encoding a gene ortholog from the family or genus of the seed plant species into which the nucleic acid molecule is to be introduced is preferred for generating a non-naturally occurring seed plant of the invention using homologous recombination, cosuppression or antisense technology. More preferably, a nucleic acid molecule encoding a gene ortholog from the same seed plant species is used for suppressing AGL8-related gene product expression in a seed plant of the invention. For example, a nucleic acid molecule encoding a canola AGL8-related gene product such as canola AGL8 is preferable for suppressing AGL8-related gene product expression in a canola plant.

Although use of a highly homologous nucleic acid molecule is preferred in the methods of the invention, the nucleic acid molecule to be used for homologous recombination, cosuppression or antisense suppression need not contain in its entirety the AGL8-related gene product sequence to be suppressed. Thus, a sense or antisense nucleic acid molecule encoding only a portion of Arabidopsis AGL8 (SEQ ID NO:2), for example, can be useful for producing a non-naturally occurring seed plant of the invention, in which AGL8-related gene product expression is suppressed.

A portion of a nucleic acid molecule to be homologously recombined generally contains at least about 1 kb of sequence homologous to the targeted gene and preferably contains at least about 2 kb, more preferably at least about 3 kb and can contain at least about 5 kb of sequence homologous to the targeted gene. A portion of a nucleic acid molecule encoding an AGL8-related gene product to be used for cosuppression or antisense suppression generally contains at least about 50 base pairs to the full-length of the nucleic acid molecule encoding the AGL8-related gene product. In contrast to an active segment, as defined herein, a portion of a nucleic acid molecule to be used for homologous recombination, cosuppression or antisense suppression need not encode a functional part of a gene product.

A dominant negative construct also can be used to suppress AGL8-related gene product expression in a seed plant. A dominant negative construct useful in the invention generally contains a portion of the complete AGL8-related gene product coding sequence sufficient, for example, for DNA-binding or for a protein-protein interaction such as a homodimeric or heterodimeric protein-protein interaction but lacking the transcriptional activity of the wild type protein. For example, a carboxy-terminal deletion mutant of AGAMOUS was used as a dominant negative construct to suppress expression of the MADS box gene AGAMOUS (Mizukami et al., *Plant Cell* 8:831–844 (1996), which is incorporated by reference herein). One skilled in the art understands that, similarly, a dominant negative AGL8-related-gene product construct, such as a dominant negative AGL8 ortholog construct can be used to suppress the expression of an AGL8-related gene product in a seed plant, thereby resulting in production of seeds of decreased size. A useful dominant negative construct can be a deletion mutant encoding, for example, the MADS box domain alone ("M"), the MADS box domain and "intervening" region ("MI"); the MADS box, "intervening" and "K" domains ("MIK"); or the "intervening," "K" and carboxy-terminal domains ("IKC").

A seed plant characterized by producing seeds of decreased size also can be produced by manipulating expression of AGL1 and AGL5. Suppression of AGL8-related gene product expression can be achieved indirectly by suppression of AGL1 and AGL5 expression in the seed plant. A non-naturally occurring seed plant in which expression of an AGL8-related gene product is suppressed can be, for example, an agl1 agl5 double mutant. As used herein, the term "agl1 agl5 double mutant" means a seed plant having a loss-of-function mutation at the AGL1 locus and a loss-of-function mutation at the AGL5 locus. Loss-of-function mutations encompass point mutations, including substitutions, deletions and insertions, as well as gross modifications of an AGL1 and AGL5 locus and can be located in coding or non-coding sequences. One skilled in the art understands that any such loss-of-function mutation at the AGL1 locus can be combined with any such mutation at the AGL5 locus to generate an agl1 agl5 double mutant of the invention. Production of an exemplary agl1 agl5 double mutant in the Brassica seed plant Arabidopsis is described in Kempin et al., *Nature* 389:802–803 (1997), which is incorporated herein by reference.

AGL1 and AGL5 are closely related genes that have diverged relatively recently. While not wishing to be bound by the following, some plants can contain only AGL1 or only AGL5, or can contain a single ancestral gene related to AGL1 and AGL5. In such plants, a seed plant characterized by producing seeds of decreased size can be produced by suppressing only expression of AGL1, or expression of AGL5, or expression of a single ancestral gene related to AGL1 and AGL5. Thus, in some plant species, a non-naturally occurring seed plant characterized by producing seeds of decreased size due to suppression of AGL8-related gene product expression can be a plant in which AGL1 expression is suppressed. Such a non-naturally occurring seed plant characterized by producing seeds of decreased size due to suppression of AGL8-related gene product expression can be, for example, an agl1 single mutant. Similarly, in some plant species, a non-naturally occurring seed plant characterized by producing seeds of decreased size due to suppression of AGL8-related gene product expression, can be a plant in which AGL5 expression is suppressed. Such a plant can be, for example, an agl5 single mutant.

Kits for generating a transgenic seed plant characterized by producing seeds of increased size also are provided herein. The kits of the invention include a nucleic acid molecule encoding an AGL8-related gene product and a seed-selective regulatory element. In a kit of the invention, the AGL8-related gene product can have, for example, substantially the amino acid sequence of an AGL8 ortholog. If desired, a kit for generating a transgenic seed plant characterized by producing seeds of increased size can include a plant expression vector containing a nucleic acid molecule encoding an AGL8-related gene product operatively linked to a seed-selective regulatory element.

Nucleic acid molecules encoding AGL8-related gene products, such as those having substantially the amino acid sequence of an AGL8 ortholog, have been described hereinabove. A kit of the invention can contain one of a variety of nucleic acid molecules encoding AGL8-related gene products and any seed-selective regulatory element, such as an element described hereinabove.

If desired, a kit of the invention also can contain a plant expression vector. As used herein, the term "plant expression vector" means a self-replicating nucleic acid molecule that provides a means to transfer an exogenous nucleic acid molecule into a seed plant host cell and to express the molecule therein. Plant expression vectors encompass vectors suitable for Agrobacterium-mediated transformation, including binary and cointegrating vectors, as well as vectors for physical transformation.

Plant expression vectors can be used for transient expression of the exogenous nucleic acid molecule, or can integrate and stably express the exogenous sequence. One skilled in the art understands that a plant expression vector can contain all the functions needed for transfer and expression of an exogenous nucleic acid molecule; alternatively, one or more functions can be supplied in trans as in a binary vector system for Agrobacterium-mediated transformation.

In addition to containing a nucleic acid molecule encoding an AGL8-related gene product operatively linked to a seed-selective regulatory element, a plant expression vector of the invention can contain, if desired, additional elements. A binary vector for Agrobacterium-mediated transformation contains one or both T-DNA border repeats and can also contain, for example, one or more of the following: a broad host range replicon, an ori T for efficient transfer from $E.\ coli$ to Agrobacterium, a bacterial selectable marker such as ampicillin and a polylinker containing multiple cloning sites.

A plant expression vector for physical transformation can have, if desired, a plant selectable marker and can be based on a vector such as pBR322, pUC, pGEM and M13, which are commercially available, for example, from Pharmacia (Piscataway, N.J.) or Promega (Madison, Wis.). In plant expression vectors for physical transformation of a seed plant, the T-DNA borders or the ori T region can optionally be included but provide no advantage.

As disclosed herein, overexpression of AGL8 in Arabidopsis results in the production of fruit that are larger in size than fruit produced by wild type Arabidopsis (see Example II). While wild type Arabidopsis produced fruit that was about ¾" long and about ⅛" wide, transformed Arabidopsis expressing AGL8 constitutively produced fruit that averaged about 1⅛" long. While not wishing to be bound by the following, style tissue in the 35S::AGL8 transgenic plants was converted to ovary tissue, resulting in elongation of the fruit at the expense of the style. Based on the increased fruit size observed in seed plants constitutively expressing AGL8, the invention provides a non-naturally occurring seed plant that is characterized by producing fruit of increased size due to ectopic expression of a nucleic acid molecule encoding an AGL8-family gene product. The AGL8-family gene product can have substantially the amino acid sequence of an AGL8 ortholog, for example, the amino acid sequence of Arabidopsis AGL8 (SEQ ID NO:2).

In a related embodiment, the invention provides a transgenic seed plant that is characterized by producing fruit of increased size due to ectopic expression of an exogenous nucleic acid molecule encoding an AGL8-family gene product. The exogenous ectopically expressed nucleic acid molecule encoding an AGL8-family gene product can be operatively linked to an exogenous regulatory element, which can be, for example, a constitutive regulatory element or a valve-selective regulatory element.

A tissue derived from a non-naturally occurring seed plant that is characterized by producing fruit of increased size due to ectopic expression of a nucleic acid molecule encoding an AGL8-family gene product also is provided herein. The invention provides, for example, a fruit derived from a non-naturally occurring seed plant of the invention characterized by producing fruit of increased size.

The invention also provides a method of generating a non-naturally occurring seed plant that is characterized by producing fruit of increased size. The method includes the step of ectopically expressing a nucleic acid molecule encoding an AGL8-family gene product in the seed plant, whereby fruit size is increased due to ectopic expression of the nucleic acid molecule. In one embodiment, the method includes the step of introducing an exogenous nucleic acid molecule encoding an AGL8-family gene product into the seed plant.

A non-naturally occurring seed plant of the invention characterized by producing fruit of increased size is any fruit-bearing seed plant, for example, a member of the Brassicaceae, a member of the Fabaceae, or a cereal plant, such as a corn plant, rice plant, or small grain cereal plant such as a barley, wheat, oat or rye plant.

Other examples of a non-naturally occurring seed plant of the invention characterized by producing fruit of increased size include citrus trees, such as orange trees, grapefruit trees, lemon trees and lime trees. A non-naturally occurring seed plant of the invention characterized by producing fruit of increased size also can be a plant that bears, for example, grapes, apples, pears, peaches, plums, cherries, bananas, blackberries, blueberries, raspberries, strawberries, pineapples, dates, avocados, olives, coconuts, tomatoes, cucumbers or eggplants, such fruits having an increased size as compared to the fruit produced by the corresponding wild type plant. Based on the observed conversion of style to ovary tissue described above, one skilled in the art understands that the methods of the invention for generating a non-naturally occurring seed plant can be particularly applicable to seed plants that bear fruits having a relatively large style. The skilled person will recognize that the invention can be practiced with these or other fruit-bearing seed plants as desired.

As used herein in reference to a fruit produced by a non-naturally occurring seed plant of the invention, the term "increased size" means a significantly greater fruit volume or dry weight as compared to the volume or dry weight of fruit produced by a corresponding seed plant lacking an ectopically expressed nucleic acid molecule encoding an AGL8-family gene product, such as a wild type seed plant.

It is recognized that there can be natural variation in the size of fruits produced by a particular seed plant species or variety. However, fruits of increased size produced by a seed plant using a method of the invention readily can be identified by sampling a population of the produced fruits and determining that the normal distribution of fruit sizes is greater, on average, than the normal distribution of seeds produced by the corresponding seed plant variety or species lacking an ectopically expressed nucleic acid molecule encoding an AGL8-family gene product. Thus, production of non-naturally occurring seed plants of the invention provides a means to skew the normal distribution of fruit sizes produced by a seed plant, such that the fruit volumes or dry weights are, on average, at least about 5% greater, 10% greater, 20% greater, 30% greater, 50% greater, 75% greater, 100% greater, 200% greater, 300% greater, 400% greater or 500% greater than in the corresponding seed plant species that does not contain an ectopically expressed nucleic acid molecule encoding an AGL8-family gene product.

As used herein, the term "AGL8-family gene product" means a gene product that has the same or similar function as Arabidopsis AGL8 such that, when ectopically expressed in a seed plant, normal development is altered such that fruits of increased size are produced. Arabidopsis AGL8 (SEQ ID NO:2) is an example of an AGL8-family gene product as defined herein. As disclosed in Example II, ectopic expression of Arabidopsis AGL8 (SEQ ID NO:2) under control of a tandem CaMV 35S promoter, in which the intrinsic promoter element has been duplicated, alters normal plant development such that fruits enlarged by about 50% as compared to fruit from wild type plants are produced.

An AGL8-family gene product generally is characterized, in part, as containing a MADS domain. An AGL8-family gene product also generally is characterized by having an amino acid sequence that has at least about 50% amino acid identity with the amino acid sequence of Arabidopsis AGL8 (SEQ ID NO:2). An AGL8-family gene product can have, for example, an amino acid sequence with greater than about 65% amino acid sequence identity with Arabidopsis AGL8 (SEQ ID NO:2), preferably greater than about 75% amino acid identity with Arabidopsis AGL8 (SEQ ID NO:2), more preferably greater than about 85% amino acid identity with Arabidopsis AGL8 (SEQ ID NO:2), and can be a sequence having greater than about 90%, 95% or 97% amino acid identity with Arabidopsis AGL8 (SEQ ID NO:2).

A nucleic acid molecule encoding an AGL8-family gene product can be ectopically expressed in a heterologous seed plant to produce a non-naturally occurring seed plant characterized by producing fruits of increase size since AGL8-family gene products such as AGL8 orthologs can be well-conserved and can function across species boundaries. Thus, ectopic expression of a nucleic acid molecule encoding Arabidopsis AGL8 (SEQ ID NO:2) in a heterologous seed plant within the Brassicaceae can alter normal development and result in production of fruits of increased size. Similarly, a nucleic acid molecule encoding Arabidopsis AGL8 (SEQ ID NO:2), for example, can be ectopically expressed in more distantly related heterologous seed plants, including dicotyledonous and monocotyledonous angiosperms and gymnosperms and, upon ectopic expression, can alter normal development such that fruits of increased size are produced by the heterologous seed plant.

As used herein, the term "AGL8-family gene product" encompasses an active segment of an AGL8-family gene product, which is a polypeptide portion of an AGL8-family gene product that, when ectopically expressed, alters normal development such that fruits of increased size are produced. An active segment can be, for example, an amino terminal, internal or carboxy terminal fragment of Arabidopsis AGL8 (SEQ ID NO:2) that, when ectopically expressed in a seed plant, alters normal development such that fruits of increased size are produced. An active segment of an AGL8-family gene product can include, for example, the MADS domain and can have the ability to bind DNA specifically. The skilled artisan will recognize that a nucleic acid molecule encoding an active segment of an AGL8-family gene product can be useful in producing a seed plant of the invention characterized by producing seeds of fruits of increased size and in the related methods and kits of the invention.

An active segment of an AGL8-family gene product can be identified using the methods described in Example II or using other routine methodology. Briefly, a seed plant such as Arabidopsis can be transformed with a nucleic acid molecule under control of a constitutive regulatory element such as a tandem CaMV 35S promoter. Phenotypic analysis of the seed plant reveals whether a seed plant ectopically expressing a particular polypeptide portion produces fruits of increased size.

An AGL8-family gene product can have "substantially the amino acid sequence" of an AGL8 ortholog, which encompasses a polypeptide or polypeptide segment having an identical amino acid sequence, or a polypeptide or polypeptide segment having a similar, non-identical sequence that is considered by those skilled in the art to be a functionally equivalent amino acid sequence. An AGL8-related gene product that has "substantially the amino acid sequence" of an AGL8 ortholog can have one or more modifications such as amino acid additions, deletions or substitutions relative to the AGL8 amino acid sequence of SEQ ID NO:2, provided that the modified polypeptide retains substantially the ability to alter normal development such that fruits of increased size are produced when the nucleic acid molecule is ectopically expressed in the seed plant.

Further provided by the invention are kits for generating a transgenic seed plant characterized by producing fruit of increased size. The kits include a nucleic acid molecule encoding an AGL8-family gene product as well as a valve-selective regulatory element. The AGL8-family gene product can have, for example, substantially the amino acid sequence of an AGL8 ortholog. If desired, a kit of the invention can include a plant expression vector containing a nucleic acid molecule encoding an AGL8-family gene product operatively linked to a valve-selective regulatory element.

As used herein, the term "valve-selective regulatory element" refers to a nucleotide sequence that, when operatively linked to a nucleic acid molecule, confers selective expression upon the operatively linked nucleic acid molecule in a limited number of plant tissues, including valve tissue. As used herein, the term valve-selective regulatory element refers to an element that can confer specific expression exclusively in valve tissue, or that can confer selective expression in a limited number of plant tissues including valve tissue.

A valve-selective regulatory element can be derived, for example, from a gene that is selectively expressed in the valve tissue of a seed plant. For example, genes selectively expressed in valve tissue of a seed plant include the gene that confers selective GUS expression in the Arabidopsis transposant line GT142 (Sundaresan et al., *Genes Devel.* 9:1797–1810 (1995), which is incorporated herein by reference). Additional valve-selective regulatory elements can be identified and isolated using routine methodology. Differential screening strategies using, for example, RNA prepared from the valve tissue and RNA prepared from non-valve tissue, such as root or leaf tissue, can be used to isolate cDNAs selectively expressed in valve tissue. Enhancer trap or gene trap strategies and expression screening of libraries, as described above in regard to the isolation of seed-selective regulatory elements, also can be used to identify additional valve-selective regulatory elements.

The invention further provides a non-naturally occurring seed plant that is characterized by producing fruit of decreased size, in which expression of an AGL8-family gene product is suppressed. Such a non-naturally occurring seed plant can be valuable for producing, for example, small cucumbers, which are prized for the preparation of certain types of pickles. In such a non-naturally occurring seed plant of the invention, an AGL8-family gene product can have, for example, substantially the amino acid sequence of an AGL8 ortholog. In one embodiment, expression of the AGL8-family gene product is selectively suppressed in valve tissue. Also provided herein is a tissue, such as a fruit, derived from a non-naturally occurring seed plant that is characterized by producing fruit of decreased size, in which expression of an AGL8-family gene product is suppressed.

The term "decreased size," as used herein in reference to a fruit produced by a non-naturally occurring seed plant of the invention, means a significantly reduced fruit volume or dry weight as compared to the volume or dry weight of fruit produced by a corresponding seed plant lacking an ectopically expressed nucleic acid molecule encoding an AGL8-family gene product such as a wild type seed plant. Fruits of decreased size can have volumes or dry weights that are, on average, less than about 9/10, 8/10, 7/10, 5/10, 3/10, 2/10 or 1/10 the volume or dry weight of the fruits produced by a corresponding wild type seed plant.

The following examples are intended to illustrate but not limit the present invention.

EXAMPLE I

Production of a 35S::AGL8 Transgenic Arabidopsis Plant Producing Seeds of Increased Size This example describes methods for producing a transgenic Arabidopsis plant with altered development such that seeds of increased size and weight are produced.

Full-length AGL8 was prepared by polymerase chain reaction amplification using primer AGL8 5-γ (SEQ ID NO:3; 5'-CCGTCGACGATGGGAAGAGGTAGGGTT-3') and primer OAM14 (SEQ ID NO:4; 5'-AATCATTACCAAGATATGAA-3'), and subsequently cloned into the SalI and BamHI sites of expression vector pBIN-JIT, which was modified from pBIN19 to include the tandem CaMV 35S promoter, a polycloning site and the CaMV polyA signal. Arabidopsis was transformed using the in plant a method of Agrobacterium-mediated transformation essentially as described in Bechtold et al., *C.R Acad. Sci. Paris* 316:1194–1199 (1993), which is incorporated herein by reference. Kanamycin-resistant lines were analyzed for the presence of the 35S-AGL8 construct by PCR using a primer specific for the 35S promoter and a primer specific for the AGL8 cDNA, which produced two fragments of 850 and 550 bp in the 35S-AGL8 transgenic plants. These fragments were absent in plants that had not been transformed with the 35S-AGL8 construct.

The phenotype of two representative and 35S::AGL8 lines with independent insertion events was analyzed. In both of the transgenic lines, it appeared that senescence was delayed, as indicated by the fact that the transgenic fruit stayed fresher longer. In particular, transgenic fruit dried about fourteen days after yellowing, while wild type fruit dried about two days after yellowing.

Further characterization of the 35S::AGL8 transgenic seed plants revealed that the seeds exhibited an increased volume and weight. The transgenic seed volumes were noticeably increased, with an increase of about 30% in each dimension as compared to control, non-transformed Arabidopsis plants. Furthermore, seeds were on average about three times as heavy as the seeds from control plants. The average size of 200 dry seeds from wild type plants was 2.6 mg, while 200 dry seeds from 35S::AGL8 line #1 weighed 7.6 mg, and 200 dry seeds from 35S::AGL8 line #2 weighed 7.7 mg.

The data set forth above indicate that ectopic expression of AGL8 can delay senescence in seed plants, keeping fruit fresher longer. Furthermore, ectopic expression of AGL8 can result in production of seeds of increased size and weight.

EXAMPLE II

Production of a 35S::AGL8 Transgenic Arabidopsis Plant Producing Fruits of Increased Size This example describes methods for producing a transgenic Arabidopsis plant that produces fruit of increased size.

Full-length AGL8 under control of a tandem CaMV 35S promoter was used to prepare 35S::AGL8 transgenic Arabidopsis plants as described above. Characterization of 35S::AGL8 transgenic Arabidopsis lines indicated that the transgenic fruit was enlarged as compared to fruit from wild type plants. Where wild type Arabidopsis produced fruit that was about ¾" long and about ⅛" wide, transformed Arabidopsis constitutively expressing AGL8 produced fruit that averaged 1⅛" in length. The increased fruit length can be attributed to the conversion of style tissue to ovary tissue.

The results described above indicate that ectopic expression of AGL8, such as constitutive AGL8 expression, can result in production of fruit of a significantly larger size as compared to the fruit produced by wild type plants.

EXAMPLE III

AGL8 Interacts with AGL5 in Yeast

This example demonstrates that, in a yeast two-hybrid system, the AGL8 gene product interacts with AGL5.

The "interaction trap" of Finley and Brent (*Gene Probes: A Practical Approach* (1994); see, also Gyuris et al., *Cell* 75:791–803 (1993)) is a variation of the yeast two-hybrid system of Fields and Song, *Nature* 340:245–246 (1989). In this system, a first protein is fused to a DNA-binding domain, and a second is fused to a transcriptional activation domain. An interaction between the Arabidopsis AGL5 and AGL8 gene products was assayed by activation of a lacZ reporter gene.

The "bait" and "prey" constructs were prepared in single copy centromere plasmids pBI-880 and pBI-771, respectively, which each contain the constitutive ADH1 promoter and are essentially as described by Chevray and Nathans, *Proc. Natl. Acad. Sci. USA* 89:5789–5793 (1992). The bait construct contains the GAL4 DNA-binding domain (amino acids 1 to 147) fused to the full-length AGL8 coding sequence. The prey construct has the full-length coding sequence of AGL5 fused to the GAL4 transcriptional activation domain (amino acids 768–881), following a nuclear localization sequence. The bait and prey constructs were assayed in the YPB2 strain of *S. cerevisiae*, which is deficient for GAL4 and GAL80 and which contains an integrated lacZ reporter gene under control of GAL1 promoter elements (Feilotter et al., *Nucleic Acids Research* 22:1502–1503 (1994)).

An interaction of the AGL8 "bait" and AGL5 "prey" was demonstrated in the YPB2 strain by the development of blue colonies on X-GAL containing media. Control "bait"-"prey" combinations, including the GAL4(1–147) DNA binding domain and GAL4 transcriptional activation domain only produced only white colonies. These results demonstrate that AGL8 can interact with AGL5 in yeast and indicate that the AGL8 and AGL5 plant MADS box gene products also can interact in seed plants.

All journal article, reference, and patent citations provided above, in parentheses or otherwise, whether previously stated or not, are incorporated herein by reference.

Although the invention has been described with reference to the examples above, it should be understood that various modifications can be made without departing from the spirit of the invention. Accordingly, the invention is limited only by the following claims.

We claim:

1. A transgenic seed plant comprising an exogenous nucleic acid under the control of a regulatory element, wherein the nucleic acid encodes a protein having greater than 50% amino acid identity to SEQ ID NO: 2, and wherein the seed plant produces seeds of decreased size.

2. The transgenic seed plant of claim 1, wherein the protein has greater than 90% amino acid identity with SEQ ID NO:2.

3. The transgenic seed plant of claim 1, wherein the exogenous nucleic acid molecule is in a sense orientation relative to the regulatory element.

4. The transgenic seed plant of claim 1, wherein the exogenous nucleic acid molecule is in an antisense orientation relative to the regulatory element.

5. The transgenic seed plant of claim 1, wherein the protein has the amino acid sequence of Arabidopsis AGL8 (SEQ ID NO:2).

6. The transgenic seed plant of claim 1, wherein the exogenous nucleic acid molecule encoding the protein is operatively linked to an exogenous regulatory element.

7. The transgenic seed plant of claim 6, wherein the regulatory element is a constitutive regulatory element.

8. The transgenic seed plant of claim 6, wherein the regulatory element is a cauliflower mosaic virus 35S promoter.

9. The transgenic seed plant of claim 6, wherein the regulatory element is a seed-selective regulatory element.

10. The transgenic seed plant of claim 6, wherein the regulatory element is a valve-selective regulatory element.

11. A transgenic tissue from the transgenic seed plant of claim 1.

12. The tissue of claim 11, which is a seed.

13. A method of producing a plant that produces seeds of decreased size, the method comprising introducing into the plant an exogenous nucleic acid molecule under the control of a regulatory element, wherein the nucleic acid encodes a protein having at least 75% amino acid identity to SEQ ID NO:2, thereby producing a plant that produces seeds of decreased size.

14. The method of claim 13, wherein the protein has greater than 90% amino acid identity with SEQ ID NO:2.

15. The method of claim 13, wherein said regulatory element is a constitutive regulatory element.

16. The method of claim 13, wherein said regulatory element is a cauliflower mosaic virus 35S promoter.

17. The method of claim 13, wherein said regulatory element is a seed-selective regulatory element.

18. The method of claim 13, wherein said regulatory element is a valve-selective regulatory element.

* * * * *